United States Patent [19]

Herzig et al.

[11] Patent Number: 5,576,445
[45] Date of Patent: Nov. 19, 1996

[54] INTERMEDIATES FOR REACTIVE DYES

[75] Inventors: Paul Herzig, Basel; Anton Andreoli, Riehen, both of Switzerland

[73] Assignee: Ciba-Geigy Corporation, Tarrytown, N.Y.

[21] Appl. No.: 451,355

[22] Filed: May 26, 1995

[30] Foreign Application Priority Data

May 30, 1994 [CH] Switzerland ............................ 1678/94

[51] Int. Cl.⁶ .................................................. C07D 209/48
[52] U.S. Cl. ............................ 548/477; 548/478; 548/113
[58] Field of Search ................................... 548/477, 478, 548/113

[56] References Cited

U.S. PATENT DOCUMENTS 2,533,178  12/1950  Randall et al. ........................ 260/326
3,867,406  2/1975  Schwantje ............................. 260/326 D
4,769,446  9/1988  Carso et al. .............................. 534/642
5,003,052  3/1991  Tzikas .................................... 534/641

FOREIGN PATENT DOCUMENTS 1561420  2/1980  United Kingdom .

*Primary Examiner*—Patricia L. Morris
*Attorney, Agent, or Firm*—Kevin T. Mansfield

[57] ABSTRACT

Compounds of the formula

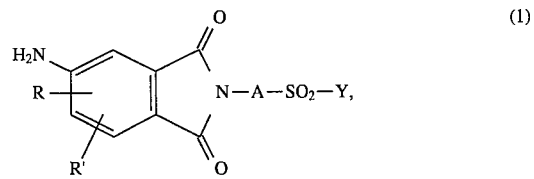

in which the variables are as defined in the claims and which are suitable diazo components for the synthesis of fibre-reactive dyes are described.

8 Claims, No Drawings

INTERMEDIATES FOR REACTIVE DYES

The present invention relates to novel intermediates for the preparation of reactive dyes and to processes for their preparation.

A large number of fibre-reactive dyes, processes for their preparation and suitable intermediates for their synthesis are known. In view of the ever higher requirements of reactive dyeings in respect of profitability, application technique and level of fastness, however, the state of the art achieved is often not yet completely satisfactory. The synthesis of novel reactive dyes, however, is associated to a considerable degree with the discovery of novel suitable intermediates. There is therefore a need for novel intermediates which can serve as the starting point for the synthesis of novel reactive dyes having improved properties.

Surprisingly, novel phthalimide compounds which are valuable intermediates for the synthesis of reactive dyes have now been found.

The present invention accordingly provides compounds of the formula

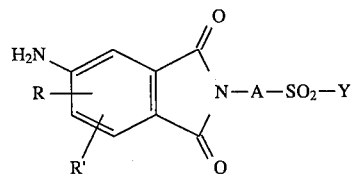

(1)

in which
R and R' independently of one another are each hydrogen, sulfo, hydroxyl, $C_1$–$C_4$alkoxy, halogen or cyano,
A is $C_1$–$C_6$alkylene which is unsubstituted or substituted by halogen, hydroxyl, sulfato, carboxyl, cyano, $C_2$–$C_4$alkanoyloxy, $C_1$–$C_4$alkoxycarbonyl or carbamoyl or interrupted by a group —O— or —$NR_1$—, or is $C_1$–$C_6$alkylenephenylene which is unsubstituted or substituted in the phenyl part by $C_1$–$C_4$alkyl, $C_1$–$C_4$alkoxy, halogen or sulfo,
$R_1$ is hydrogen or $C_1$–$C_4$alkyl,
Y is vinyl or a radical —$CH_2$—$CH_2$—U and
U is a leaving group which can be split off under alkaline conditions.

The term sulfo here generally includes both the free acid —$SO_3H$ and any salt form, for example an alkali metal, alkaline earth metal or ammonium salt or the salt of an organic amine, such as the sodium, potassium, lithium or ammonium salt or the salt of triethanolamine.

$C_1$–$C_4$Alkyl is generally methyl, ethyl, n- or iso-propyl or n-, iso-, sec- or tert-butyl. $C_1$–$C_4$Alkoxy is generally methoxy, ethoxy, n- or iso-propoxy or n-, iso-, sec- or tert-butoxy, and preferably methoxy or ethoxy. Halogen is generally, for example, bromine or chlorine. Examples of $C_2$–$C_4$alkanoyloxy are acetyl or propionyl, and examples of $C_1$–$C_4$alkoxycarbonyl are methoxycarbonyl or ethoxycarbonyl. $C_1$–$C_6$Alkylene is generally to be understood as meaning $C_1$–$C_6$alkylene which is straight-chain or branched in any manner; examples are methylene, 1,1- or 1,2-ethylene, 1,2- or 1,3-propylene, 1,2-, 1,3-, 1,4- or 2,3-butylene, 1,4-, 2,3- or 2,4-pentylene, 2-methyl-1,5-pentylene and 1,6-hexylene, it being possible for these radicals to be substituted as stated or, with the exception of methylene, interrupted by a heteroatom —O— or —$NR_1$—.

R and R' independently of one another are each preferably hydrogen, sulfo, chlorine, bromine, hydroxyl, methoxy or cyano; particularly preferably, R is hydrogen, sulfo, chlorine, bromine or cyano and R' is hydrogen; especially preferably, R is hydrogen or sulfo and R' is hydrogen. A particularly preferred embodiment of the invention relates to compounds of the formula (1) in which R and R' are each hydrogen.

A $C_1$–$C_6$alkylenephenylene radical A is preferably methylenephenylene or ethylenephenylene which are unsubstituted or substituted in the phenyl part by methyl, methoxy, chlorine or sulfo, and particularly preferably methylenephenylene.

A is preferably an unsubstituted $C_1$–$C_6$alkylene radical or a radical of the formula

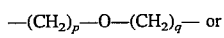

in which p and q independently of one another are each an integer from 1 to 6.

A is particularly preferably a $C_2$–$C_4$alkylene radical or a radical of the formula

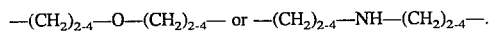

A is especially preferably 1,2-ethylene, 1,3-propylene, 1,4-butylene or a radical of the formula

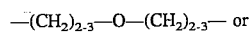

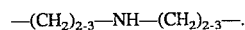

A particularly preferred embodiment of the present invention relates to compounds of the formula (1) in which A is 1,2-ethylene, 1,3-propylene or a radical of the formula —$(CH_2)_2$—O—$(CH_2)_2$—.

Suitable leaving groups U which can be split off under alkaline conditions are, for example, halogen, such as chlorine or bromine, acyloxy, such as acetoxy or benzoyloxy, phosphato, sulfato or thiosulfato.

Examples of suitable radicals Y are accordingly vinyl, β-bromo- or β-chloroethyl, β-acetoxyethyl, β-benzoyloxyethyl, β-phosphatoethyl, β-sulfatoethyl and β-thiosulfatoethyl. Y is preferably vinyl or β-sulfatoethyl.

Compounds which are of particular interest are those of the abovementioned formula (1) in which
R is hydrogen, sulfo, chlorine, bromine or cyano;
R' is hydrogen;
A is unsubstituted $C_1$–$C_6$alkylene or a radical of the formula

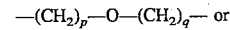

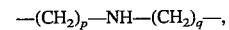

in which p and q independently of one another are each an integer from 1 to 6; and
Y is vinyl, β-bromo- or β-chloroethyl, β-acetoxyethyl, β-benzoyloxyethyl, β-phosphatoethyl, β-sulfatoethyl or β-thiosulfatoethyl.

Compounds which are of special interest are those of the abovementioned formula (1) in which
R is hydrogen or sulfo;
R' is hydrogen;
A is $C_2$–$C_4$alkylene or a radical of the formula

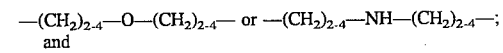
and

Y is vinyl or β-sulfatoethyl.

A particularly preferred embodiment of the present invention provides compounds of the abovementioned formula (1) in which
R and R' are each hydrogen,
A is 1,2-ethylene, 1,3-propylene or a radical of the formula —$(CH_2)_2$—O—$(CH_2)_2$— and Y is β-sulfatoethyl.

The compounds of the formula (1) can be obtained, for example, by a) reacting phthalic anhydride with a compound of the formula

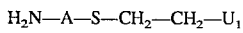  (2)

to give the compound of the formula

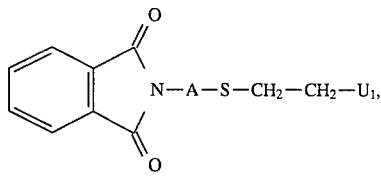  (3)

in which A is in each case as defined and preferred above and $U_1$ independently has the meaning assigned above to U or is hydroxyl, b) oxidizing the thioether compound of the formula (3) to give the corresponding sulfonyl compound of the formula

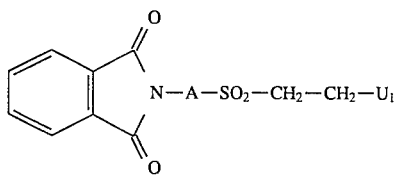  (3a)

c) selectively nitrating the resulting compound of the formula (3a) to give the compound of the formula

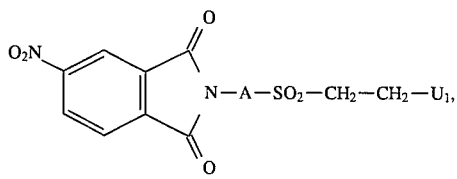  (3b)

d) reducing the resulting compound of the formula (3b) to give the amino compound of the formula

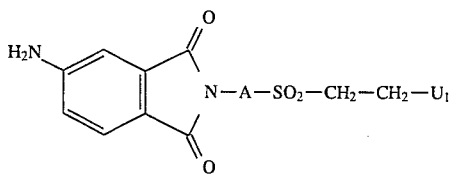  (3c)

and, if appropriate, during or after the synthesis of the compound of the formula (3a), (3b) or (3c), introducing one of the abovementioned radicals R and/or R' into the molecule or converting the radical $U_1$ into any radical U.

The condensation of phthalic anhydride with the amine of the formula (2) in step a) is carried out, for example, in an aqueous or aqueous-organic medium at a temperature of about 40° to 200° C., and preferably 50° to 150° C., under normal pressure, the water formed being distilled off.

The oxidation of the thioether compound of the formula (3) to give the sulfonyl compound of the formula (3a) in step b) can be carried out by various methods, for example with hydrogen peroxide with or without the addition of tungsten compounds or vanadium compounds as a catalyst, and furthermore with peracetic acid, potassium permanganate or chromic acid, or with chlorine/hydrochloric acid, in each case in an aqueous, aqueous-organic or organic medium.

The nitration of the compound of the formula (3a) to give the compound of the formula (3b) in step c) advantageously takes place in a mixture of concentrated sulfuric acid and concentrated nitric acid at room temperature or somewhat higher, for example at a temperature of 10° to 100° C., or preferably 30° C. to 50° C.

The reduction of the nitro compound of the formula (3b) to give the amino compound of the formula (3c) in step d) is carried out, for example, by catalytic hydrogenation with Pd/carbon in an aqueous, aqueous-organic or organic medium at room temperature up to about 60° C.; if the medium used for the hydrogenation comprises organic solvents, these are, in particular, alcohols, such as ethanol, and ethyl acetate or tetrahydrofuran. The hydrogenation mixture can also comprise a buffer, for example an acetic acid/acetate buffer. The reduction can also be carried out with Fe/hydrochloric acid or Fe/acetic acid in aqueous solution.

The compounds of the formula (3c) in which $U_1$ is hydroxyl can be converted into the corresponding compounds of the formula (1) in which Y is a radical —$CH_2$—$CH_2$—U by treatment with sulfating agents, phosphorylating agents, halogenating agents or alkyl- or arylcarboxylic acid halides, such as benzoyl chloride or acetyl chloride.

Suitable sulfating agents are, for example, concentrated sulfuric acid, and chlorosulfonic acid and amidosulfonic acid or other compounds which donate $SO_3$. The sulfation of the hydroxyl group $U_1$ to the sulfato group U can also be carried out in the course of the synthesis of the compounds of the formula (3c), for example in the nitrating step c). Halogenating agents which can be used are, for example, thionyl chloride or thionyl bromide. Suitable phosphorylating agents are, for example, concentrated phosphoric acid, pyro-, meta- or polyphosphoric acid, phosphoric acid alkyl esters, phosphorus oxytrichloride or mixtures of phosphoric acid and phosphorus(V) oxide.

If a radical R or R' is introduced into the compound of the formula (3c), sulfonation or halogenation, i.e. the introduction of a sulfo or halogen group, for example, can be carried out, this taking place in a manner known per se, for example with concentrated sulfuric acid, oleum or chlorosulfonic acid or with chlorine or bromine in the presence of Lewis acids. The compounds of the formula (1) where R and/or R'=sulfo or halogen can in turn be used as starting products for synthesis of the corresponding compounds where R and/or R'=hydroxyl, $C_1$-$C_4$alkoxy or cyano, which can be carried out by customary methods described in textbooks on organic chemistry.

The compounds of the formula (1) are valuable novel aromatic amines which can be diazotized in the customary manner, for example by the action of nitrous acid in aqueous-mineral acid solution at a low temperature, and can then be coupled with any coupling components in the acid, neutral or weakly alkaline pH range. The novel mono- or polyazo dyes thereby obtained are fibre-reactive, i.e. they are capable of reacting with the hydroxyl groups of cellulose or with the reactive centres of natural and synthetic polyamides to form covalent chemical bonds, and produce dyeings and prints having good all round fastness properties, in particular good light and wet fastness properties, on the fibre materials mentioned.

The present invention also relates to mixtures of compounds comprising in each case a compound of the formula

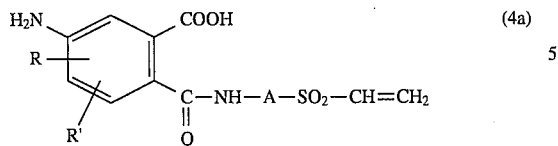

(4a)

and

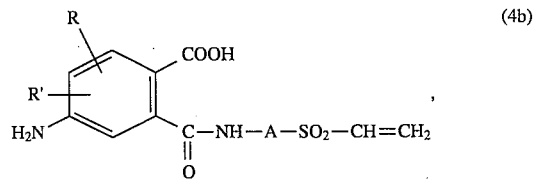

(4b)

in which A, R and R' are each as defined and preferred above; the mixtures of compounds mentioned are likewise valuable novel intermediates for the synthesis of fibre-reactive dyes for cellulose and polyamide fibre materials, and can be obtained, for example, by simple treatment of a compound of the formula (1) according to the invention in an aqueous alkaline medium. The alkaline medium has a pH of 8–14, and preferably 9–12, for example, and can be prepared by means of customary bases, for example sodium hydroxide. On treatment of the compounds of the formula (1) in such an alkaline medium, ring opening occurs, the components of the formula (4a) and (4b) in general being obtained in a stoichiometric ratio, i.e. in a ratio of about 1:1.

The following examples serve to illustrate the invention. The temperatures are in degrees Celsius, parts are parts by weight and percentage data are % by weight, unless stated otherwise. Parts by weight bear the same relation to parts by volume as the kilogram to the liter.

EXAMPLE 1

148 parts of phthalic anhydride are introduced into a solution of 121 parts of 2-amino-2'-hydroxy-diethyl sulfide in 121 parts of water. During this operation, the temperature is allowed to rise to 50° C. After the introduction, the resulting suspension is heated under reflux and the water formed is distilled off under normal pressure. The temperature is then increased to 150° C. and the mixture is stirred at this temperature for a further hour. A melt of N-(2-(2-hydroxyethylthio)ethyl)phthalimide of the formula

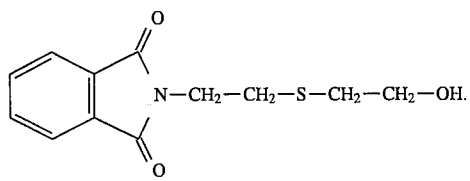

is obtained.

The resulting melt is cooled to 80° C. and 8 parts of sodium acetate and 0.5 part of tungsten(VI) oxide are then added. 214 parts of 35% hydrogen peroxide are now added dropwise at a temperature of 75°–80° C. in the course of 2 hours, and the mixture is subsequently stirred at 80° C. with a slight excess of peroxide for a further 2 hours, until sulfoxide is no longer detected by HPLC. To precipitate the emulsion formed, the hot reaction mass is poured onto 500 parts of cold water and filtered and the residue is washed free from peroxide with water. After drying in vacuo at 60° C., 253 parts of N-(2-(2-hydroxyethylsulfonyl)ethyl)phthalimide of the formula

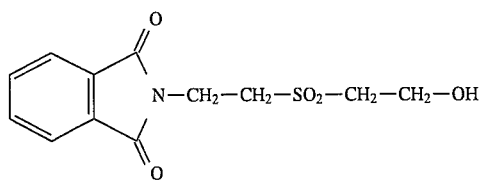

are obtained with a melting point of 120°–122° C. and a purity (HPLC) of 99%.

$^1$H-NMR analysis (measured in DMSO-$d_6$ with TMS as the standard): 3.30 ppm (2H;t), 3.50 ppm (2H;t), 3.79 ppm (2H;q), 4.05 ppm (2H;t), 5.17 ppm (1H;t), 7.8–7.9 ppm (4H).

EXAMPLE 2

253 parts of N-(2-(2-hydroxyethylsulfonyl)ethyl)phthalimide are introduced into 735 parts of 100% sulfuric acid at 20°–30° C., while stirring. The mixture is subsequently stirred at room temperature for one hour until the solution is complete. 113 parts of 50% mixed acid are now added dropwise at a temperature of 10°–15° C. in the course of 3 hours. Thereafter, the mixture is heated to 40° C. and subsequently stirred at this temperature for a further 12 hours. For isolation, the nitration mixture is poured onto 2500 parts of ice at a maximum of 5° C. 250 parts of potassium sulfate are added to the clear solution and the mixture is stirred at 10° C. for one hour. The product which has precipitated out is filtered off and washed with 10% potassium sulfate solution. 1195 parts of moist 4-nitro-N-(2-(2-sulfatoethylsulfonyl)ethyl)phthalimide of the formula

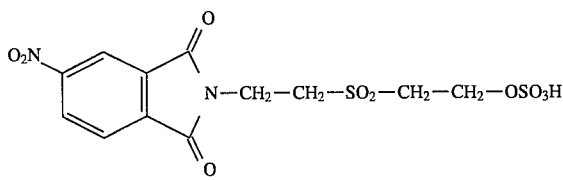

are obtained.

$^1$H-NMR analysis (measured in DMSO-$d_6$ with TMS as the standard): 3.45 ppm (2H, t); 3.50ppm (2H, t); 4.05 ppm (2H, t); 4.10 ppm (2H, t); 8.16 ppm (1H, d); 8.52 ppm (1H, 8.63 ppm (1H, d).

EXAMPLE 3

1195 parts of moist 4-nitro-N-(2-(2-sulfatoethylsulfonyl)ethyl)phthalimide are dissolved in 2500 parts of water, 10 parts of sodium acetate and 8 parts of acetic acid. This solution is hydrogenated under normal pressure at 50° C. with hydrogen, with the addition of 30 parts of 5% palladium-charcoal, until the reaction stops. After the catalyst has been filtered off, 700 parts of potassium chloride are added to the resulting solution and the product which has precipitated out is filtered off with suction. After drying in vacuo at 50° C., 150 parts of 78% (nitrite titre) 4-amino-N-(2-(2-sulfatoethylsulfonyl)ethyl)phthalimide of the formula

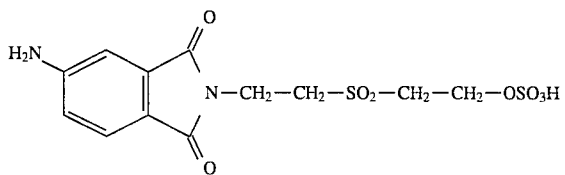

5 are obtained with a purity of 96% (HPLC).

$^1$H-NMR analysis (measured in DMSO-$d_6$ with TMS as the standard): 3.42 ppm (2H;t), 3.48 ppm (2H;t), 3.94 ppm (2H;t), 4.07 ppm (2H;t), 6.45 ppm (2H;s), 6.80 ppm (1H;q) $^3$J=7 Hz and $^4$J=2 Hz, 6.93 ppm (1H;d) $^4$J=2 Hz, 7.48 ppm (1H,d) $^3$J=7Hz.

EXAMPLES 4–6a

The following compounds can be prepared in a manner analogous to that described in Examples 1–3:

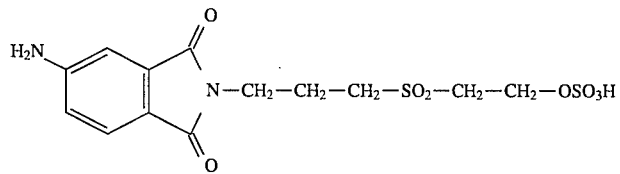

4

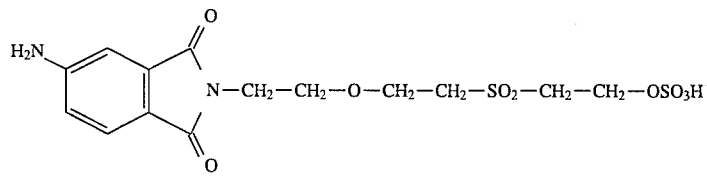

5

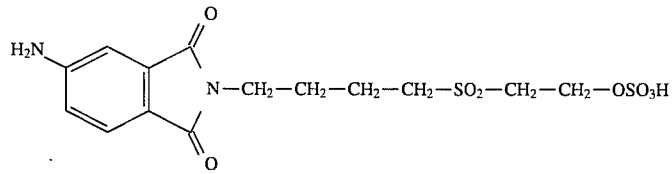

6

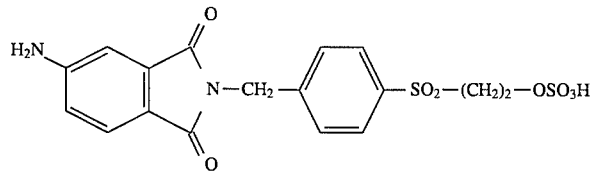

6a

EXAMPLES 7–10a

If the compounds obtained according to Examples 3 to 6a are treated for about 1 hour at room temperature in an aqueous solution, the pH of which is brought to about 10 by addition of sodium hydroxide solution, and the pH is then lowered to 6 with acetic acid, an approximately stoichiometric mixture of two compounds of the formula shown in the table, in which the amino group is in the 4-position in one case and in the 5-position in one case, is obtained.

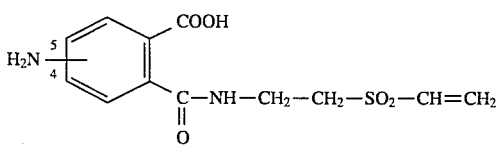

7

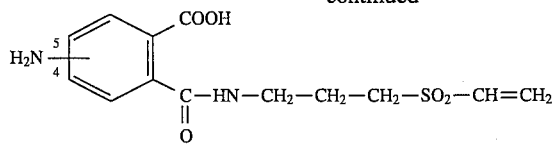

8

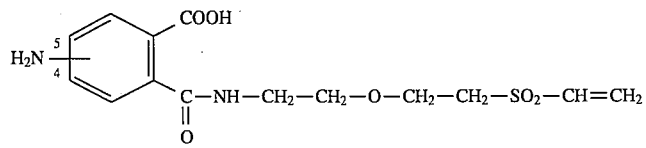

9

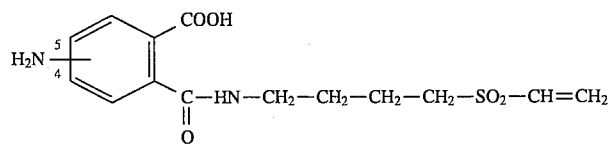

10

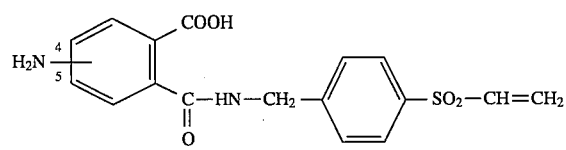

10a

EXAMPLE 11

32 parts of 65% oleum are added dropwise to 215 parts of 100% sulfuric acid at 20° to 30° C. Thereafter, 37.8 parts of the compound according to Example 3 are introduced in the course of 30 minutes, during which the temperature is allowed to rise to 60° C. The sulfonation mass is then heated at 130° C. for about 3 hours and subsequently allowed to cool to room temperature, and the cooled reaction mass is poured onto parts of ice. The excess sulfuric acid is precipitated with calcium carbonate and the pH of the filtrate resulting after the CaSO$_4$ has been filtered off is brought to a value of 4 with sodium carbonate. Evaporation or freeze drying gives the compound of the formula

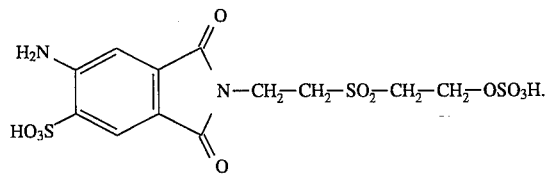

$^1$H-NMR analysis (measured in DMSO-d$_6$ with TMS as the standard): 3.45 ppm (2H;t), 3.52 ppm (2H;t), 4.03 ppm (2H;t), 4.09 ppm (2H;t), 7.03 ppm (1H;s), 7.80 ppm (1H;s).

EXAMPLE 12

If the compound obtained according to Example 11 is treated in an alkaline medium, an approximately stoichiometric mixture of two compounds of the formula

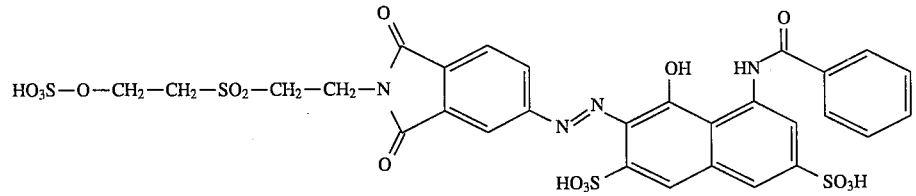

in which one compound contains the amino group in the 4-position and the sulfo group in the 5-position and the other compound contains the amino group in the 5-position and the sulfo group in the 4-position, is obtained.

EXAMPLE 13

37.8 parts of the compound according to Example 3 in 250 parts of an ice-water suspension are acidified with 25 parts by volume of 32% aqueous hydrochloric acid and diazotized with 25 parts by volume of 4N sodium nitrite solution. The mixture is subsequently stirred at a temperature of 5° C. for one hour and the excess nitrous acid is then destroyed with amidosulfonic acid. This diazonium suspension is allowed to run slowly at 0°–5° C. and a pH of 4.5–5.5 into a suspension comprising 1-benzoylamino-8-hydroxynaphthalene-3,6-disulfonic acid suspended in 200 parts of water at pH 6. During this operation, the pH is maintained by addition of sodium carbonate solution. After the addition, the mixture is subsequently stirred at pH 5.5 for a further 2 hours until coupling is complete, during which the temperature is allowed to rise to room temperature. The dye solution is then subjected to reverse osmosis and freeze-dried. A dye which, in the form of the free acid, has the formula and dyes cotton and wool in brilliant red shades with good all round fastness properties is obtained.

EXAMPLE 14

If the procedure is as in Example 13 and the pH of the reaction mixture is brought to pH 10 with 4N sodium hydroxide solution before the reverse osmosis, the mixture is stirred at this pH for one hour and the pH is then brought to pH 6 again with a little acetic acid, a dye which, in the form of the free acid, is an isomer mixture in the ratio of 1:1 of the formula

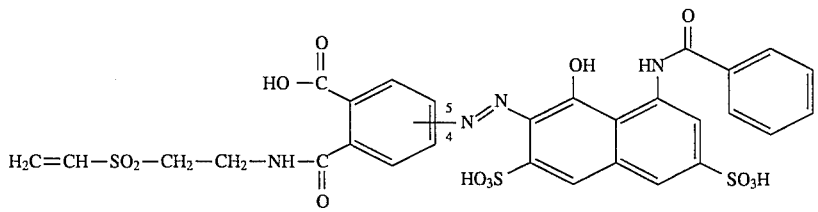

is obtained. Reverse osmosis and subsequent freeze drying gives a dye which, when used for dyeing cotton or wool, has the same properties as the dye in Example 13.

What is claimed is:

1. A compound of the formula

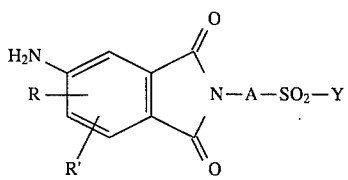

in which

R and R' independently of one another are each hydrogen, sulfo, hydroxyl, $C_1$–$C_4$alkoxy, halogen or cyano, A is $C_1$–$C_6$alkylene which is unsubstituted or substituted by halogen, hydroxyl, sulfato, carboxyl, cyano, $C_2$–$C_4$alkanoyloxy, $C_1$–$C_4$alkoxycarbonyl or carbamoyl or interrupted by a group —O— or —$NR_1$—, or is $C_1$–$C_6$alkylenephenylene which is unsubstituted or substituted in the phenyl part by $C_1$–$C_4$alkyl, $C_1$–$C_4$alkoxy, halogen or sulfo, $R_1$ is hydrogen or $C_1$–$C_4$alkyl, Y is vinyl, β-bromo- or β-chloroethyl, β-acetoxyethyl, β-benzoyloxyethyl, β-phosphatoethyl, β-sulfatoethyl or β-thiosulfatoethyl.

2. A compound according to claim 1, in which R is hydrogen, sulfo, chlorine, bromine or cyano and R' is hydrogen.

3. A compound according to claim 1, in which A is an unsubstituted $C_1$–$C_6$alkylene radical or a radical of the formula —(CH$_2$)$_p$—O—(CH$_2$)$_q$— or —(CH$_2$)$_p$—NH—(CH$_2$)$_q$—, in which p and q independently of one another are each an integer from 1 to 6.

4. A compound according to claim 1, in which A is $C_2$–$C_4$alkylene or a radical of the formula —(CH$_2$)$_{2-4}$—O—(CH$_2$)$_{2-4}$— or —(CH$_2$)$_{2-4}$—NH—(CH$_2$)$_{2-4}$—.

5. A compound according to claim 1, in which A is 1,2-ethylene, 1,3-propylene, 1,4-butylene or a radical of the formula —(CH$_2$)$_{2-3}$—O—(CH$_2$)$_{2-3}$— or

—(CH$_2$)$_{2-3}$—NH—(CH$_2$)$_{2-3}$—.

6. A compound of the formula (1) according to claim 1, in which

R is hydrogen, sulfo, chlorine, bromine or cyano,

R' is hydrogen,

A is unsubstituted $C_1$–$C_6$alkylene or a radical of the formula

—(CH$_2$)$_p$—O—(CH$_2$)$_q$— or

—(CH$_2$)$_p$—NH—(CH$_2$)$_q$—, p and q independently of one another are each an integer from 1 to 6, and Y is vinyl, β-bromo- or β-chloroethyl, β-acetoxyethyl, β-benzoyloxyethyl, β-phosphatoethyl, β-sulfatoethyl or β-thiosulfatoethyl.

7. A compound of the formula (1) according to claim 1, in which

R is hydrogen or sulfo,

R' is hydrogen,

A is $C_2$–$C_4$alkylene or a radical of the formula

—(CH$_2$)$_{2-4}$—O—(CH$_2$)$_{2-4}$— or —(CH$_2$)$_{2-4}$—NH—(CH$_2$)$_{2-4}$—, and Y is vinyl or β-sulfatoethyl.

8. A compound of the formula (1) according to claim 1, in which

R and R' are each hydrogen,

A is 1,2-ethylene, 1,3-propylene or a radical of the formula —(CH$_2$)$_2$—O—(CH$_2$)$_2$— and Y is β-sulfatoethyl.

* * * * *